United States Patent [19]
Green et al.

[11] Patent Number: 6,117,084
[45] Date of Patent: Sep. 12, 2000

[54] ULTRASONIC PROBE CONNECTOR ENCLOSURE

[75] Inventors: Dustin J. Green, Carnation; Tim Nordgren, Bothell; Wayne Heigel, Issaquah, all of Wash.

[73] Assignee: ATL Ultrasound, Inc., Bothell, Wash.

[21] Appl. No.: 09/193,656

[22] Filed: Nov. 17, 1998

[51] Int. Cl.⁷ ...................................................... A61B 8/00
[52] U.S. Cl. ............................................................ 600/459
[58] Field of Search ................................... 600/437, 438, 600/459, 460; 128/877

[56] References Cited

U.S. PATENT DOCUMENTS 5,476,107  12/1995  Oakely et al. .......................... 128/897
5,630,419   5/1997  Ranalletta .
5,678,551  10/1997  Stevens .

Primary Examiner—Marvin M. Lateef
Assistant Examiner—Maulin Patel
Attorney, Agent, or Firm—Edward A. Uhl

[57] ABSTRACT

An ultrasonic probe enclosure is provided that has a liquid tight seal for sealing an ultrasonic probe connector and a portion of an ultrasonic probe cable. The enclosure of the present invention provides liquid tight sealing in a simple and reliable manner such that the connector may be completely submersed in a sterilization liquid without causing damage to the sensitive components of the connector.

17 Claims, 6 Drawing Sheets

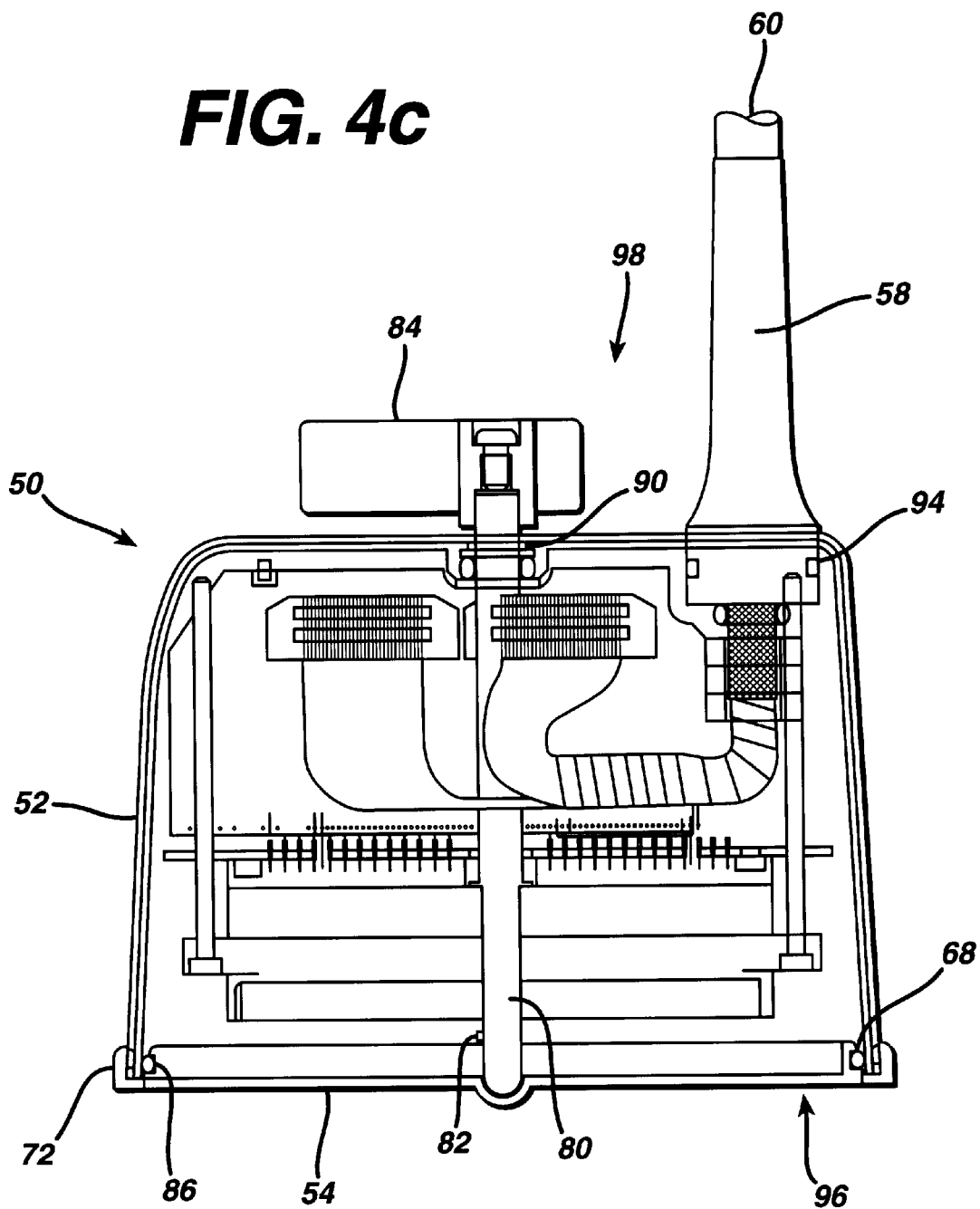

ULTRASONIC PROBE CONNECTOR ENCLOSURE

This invention relates to improvements in connector enclosures and housings for ultrasonic diagnostic imaging system probes, in particular, to connector enclosures and housings used for protecting sensitive electronic components during the sterilization process of such probes.

Ultrasonic diagnostic imaging systems are in widespread use for performing ultrasonic imaging and measurements of the human body through the use of probes which may be placed internal or external to the body being measured. Such probes are used to view the internal structure of a body with an array of transducer elements that transmits pulses or beams of energy into the body and receive returning pulses of energy as they are reflected from internal structures of the body. An ultrasonic probe assembly is typically comprised of a scan head, which houses the array of transducer elements, a multi-conductor cable, and a multi-pin connector. The pulses or beams of energy that are transmitted from and received by the array of transducer elements are electrically coupled to the ultrasonic diagnostic imaging systems by the cable and connector of the probe assembly.

Intraoperative probes are used in applications such as vascular or implant surgeries where the scanhead is placed inside the body during the surgery. To use the same probe on a different patient after a surgical procedure, the probe must be sterilized. New sterilization techniques require submersion of the probe in a liquid environment. A typical sterilization process requires the placement of the entire probe, including the connector and the cable, into a liquid tight chamber of a sterilization device. During the sterilization process, the chamber is filled with an acidic solution at an elevated temperature. The probe is then subjected to a wash cycle followed by several rinse cycles.

Since intraoperative probe connectors are comprised of moisture sensitive components, such components are subject to damage or corrosion if exposed to the liquid environment of the sterilization process. For example, the electrical characteristics of the pin connectors are important because the signals sent to and from the transducer array are carried through the connector pins. Since the transducer is comprised of multiple numbers of small piezoelectric elements that are generally made of a crystalline material, it is imperative that all of the electrical connections made to the transducer through the connector and cable are reliable. It is essential that no spurious or harmful electrical conditions be introduced or engendered, which may exist if the connector pins or other moisture sensitive components in the connector are exposed to harsh liquids. Accordingly, the sterilization techniques for intraoperative probes require the connectors to be sealed in a liquid tight manner.

To date, techniques for sealing the connectors for sterilization include the use of plugs or caps that are inserted into or over the probe connectors. Such techniques are not reliable because they tend to leak, thus exposing the sensitive electrical components of the connector to a liquid environment. Other techniques for sealing the connector include the use of a cap having a face seal that is placed over the connector pins. That technique, however, is limiting because it only operates with connectors having a specific type of connector shaft.

For example, when such a cap is connected to a connector using a connector shaft, the user must position a member of the shaft in a keyhole in the cap. As the member is rotated inside of the keyhole, the cap and face seal will be drawn into the connector. The use of a connector shaft as an integral part of sealing a connector is described in U.S. Pat. No. 5,630,419. Such devices are not reliable, however, because the connector shaft provides only a quarter of turn in rotation to draw the cap down to a sealable position. Thus, if the gasket member becomes less resilient over time or the components used to draw down the cap become worn over time, the chance of leakage increases because a greater draw cannot be provided by the connector shaft.

Other connectors have been designed to accept a cover that seals the connector for submersion in a sterilization liquid. Such connector covers, however, rely on the internal connector assembly for latching the cover to the connector housing. Such a connector is described in U.S. Pat. No. 5,678,551. One embodiment of the present invention provides a connector housing designed to accept a cover that seals the connector for submersion in a sterilization liquid without reliance on the internal connector assembly. Moreover, the devices described above may be expensive and require extensive assembly due to the multiplicity of parts. Accordingly, it is desirable to have a simple and reliable device for providing a water tight seal for an ultrasonic probe connector, such that it may be completely submersed in a sterilization liquid without causing damage to the components of the connector.

In accordance with the principles of the present invention, an ultrasonic probe connector enclosure is provided that seals the connector in a simple and reliable manner such that the connector may be completely submersed in a sterilization liquid without causing damage to the components of the connector. In a preferred embodiment the present invention is comprised of an enclosure for enclosing the connector and a portion of the connector cable in an enclosure that has a liquid tight seal.

In the drawings:

FIGS. 4a–4c illustrate top and side views of another embodiment of the present invention.

Figure 1A:
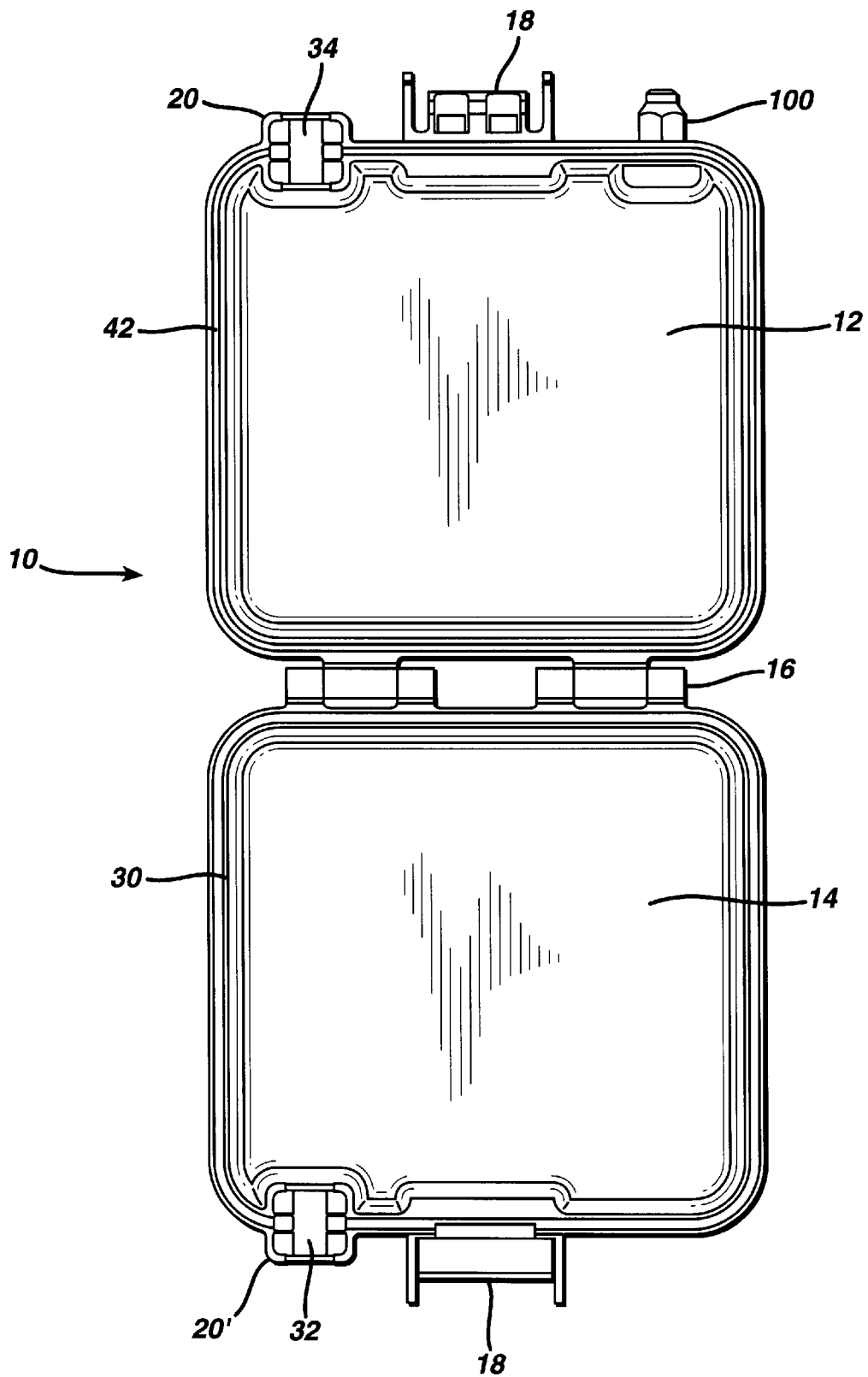
FIGS. 1a–1b illustrate a top and front view of one embodiment of the present invention.
Figure 1B:
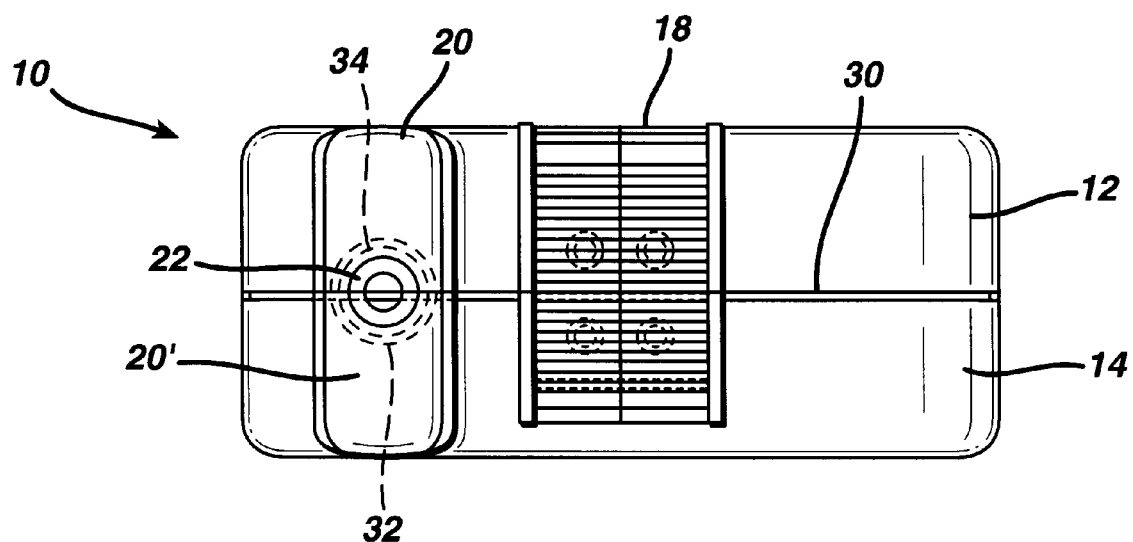

Referring first to FIGS. 1a–1b, a connector enclosure is shown that solves the problems encountered when a connector is submerged in the liquid sterilization environment by enclosing the connector and a portion of the connector cable in an enclosure that has a liquid tight seal.

As shown in FIGS. 1a–1b, the connector enclosure 10 of the present invention is comprised of a top enclosure half 12 and a bottom enclosure half 14. Top enclosure half 12 and bottom enclosure half 14 may be latched together with a common latching device 18. Enclosure halves 12 and 14 are shown connected by hinging device 16; however, a latching device may used in its place.

FIG. 1a shows a top view of connector enclosure 10 with notch 20 on top enclosure half 12. FIG. 1b shows notch 20' on bottom enclosure half 14, which is matched to mate with notch 20 when the enclosure halves are latched. FIG. 1b shows opening 22 located between notches 20 and 20' for holding and sealing the area around the probe cable. A resilient gasket 30 is also shown in FIGS. 1a–1b for providing a liquid tight seal between enclosure halves 12 and 14.

In a preferred embodiment, a check valve 100 is located on either top or bottom enclosure halve. The check valve provides the user with the ability to test gasket 30 for leaks. To test the seal, a hand pump and pressure gage are attached to an inbound port of the check valve to pressurize the enclosure to a desired pressure. The user may then observe stability of the pressure over a given time period to determine if a leak exists.

When a probe requires sterilization, the user must first orient the probe connector (not shown) into top half 12 or bottom half 14 such that the probe cable (not shown) aligns with and lays in one-half of opening 22. Once the connector and cable are properly positioned, the enclosure half without the connector may be rotated and closed over the connector by hinging device 16, and latched with latch 18. When latch 18 is latched, gasket 30, top enclosure half 12, bottom enclosure half 14, and opening 22 create a liquid tight seal around the connector and cable.

Figure 2:
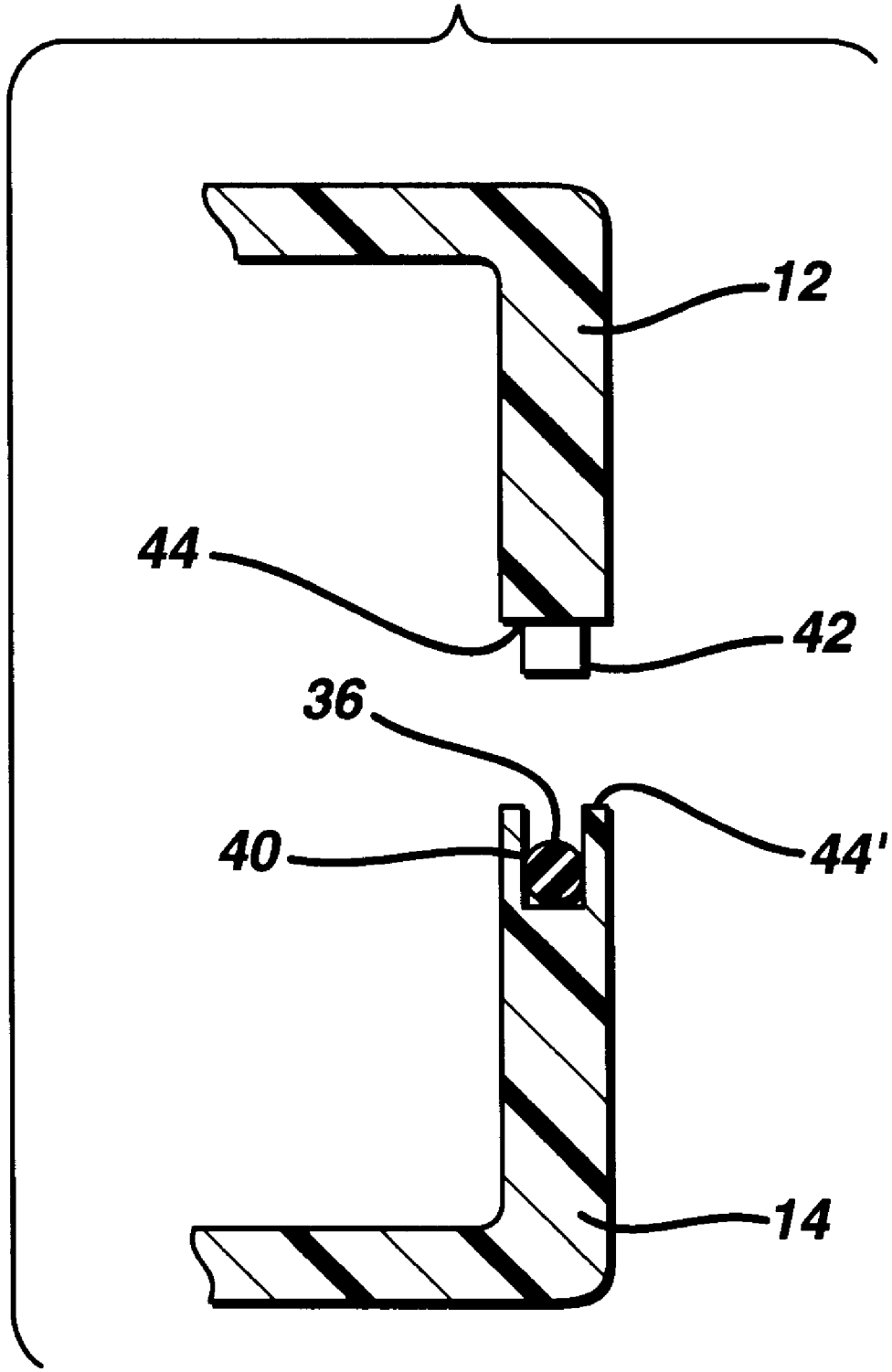
FIG. 2 illustrates in cross section a sealing technique utilized by the present invention.

Turning now to FIG. 2, groove 40 is shown in a cross section view of bottom enclosure half 14 and tongue 42 is shown in a cross section view of top enclosure half 12. Tongue 42 is located on mating surface 44 and groove 40 is located on opposing mating surface 44'. During assembly of enclosure connector 10, the body 36 of gasket 30 (See FIG. 3*a*) is positioned in groove 40. The outside diameter of body 36 is slightly larger than the diameter of groove 40 such that body 36 is snugly held in place when positioned in groove 40 (not shown). As top enclosure half 12 and bottom enclosure half 14 are latched together, body 36 is compressed between groove 40 and tongue 42 and a liquid tight seal is formed between the enclosure halves (not shown).

Figure 3A:
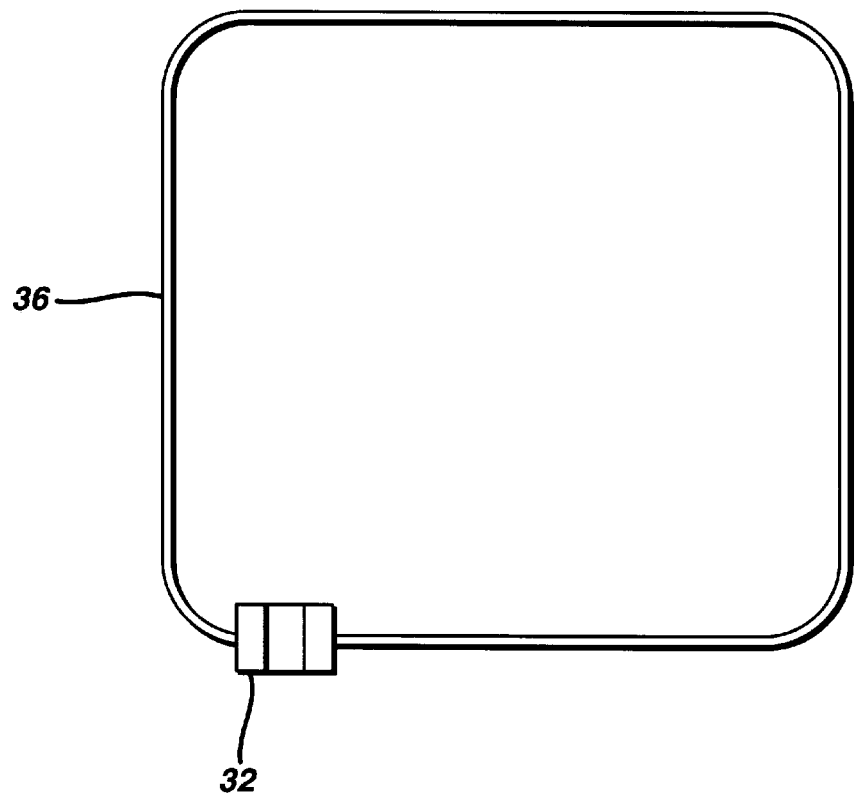
FIGS. 3a–3b illustrate top and front views of a sealing device of the present invention.
Figure 3B:
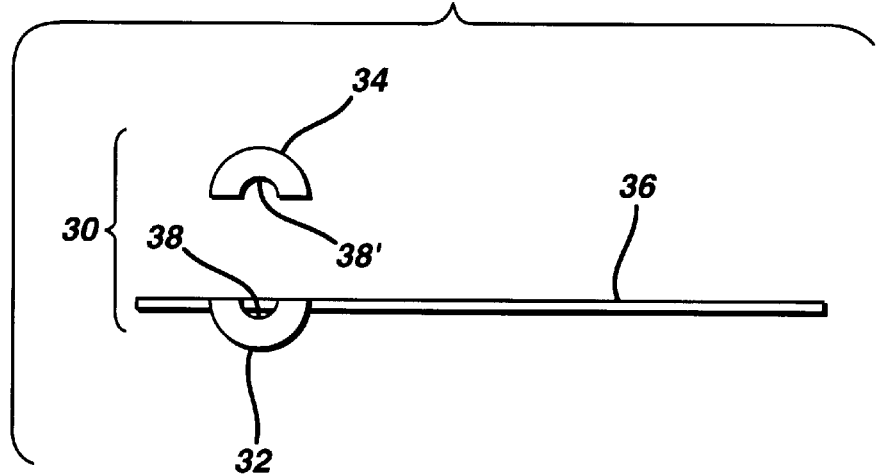

Turning now to FIGS. 3*a* and 3*b*, top and front views of gasket 30 are shown. Gasket 30 is comprised of bottom sealing portion 32, top sealing portion 34, and body 36. FIG. 3*a* shows body 36 shaped to conform to the circumference of bottom enclosure half 14. FIG. 3*a* shows bottom sealing portion 32 molded into body portion 36 such that a one piece gasket is formed. Bottom sealing portion 32 is shaped to fit snugly in notch 20' of bottom enclosure 14.

Bottom sealing portion 32 is semi-circular in shape having a solid volumetric body with an inside diameter 38 shaped to fit snugly against the cable of a probe connector (not shown). Top sealing portion 34, as shown in FIG. 3*b*, is matched in shape and size to bottom sealing portion 32 and has identical inside diameter 38'. However, top sealing portion 34 is not integrated into body 36. Rather, top portion 34 is positioned in notch 20 of top enclosure half 14 (See FIG. 1*b*). When a connector and cable are positioned in enclosure 10 and the cable is positioned in opening 22, a liquid tight seal is formed when top enclosure half 12 is latched to bottom enclosure half 14 by latch 18. Although body 36 is described as being located in bottom enclosure half 14, top enclosure half 12 may be readily configured to accept body 36.

Figure 4A:
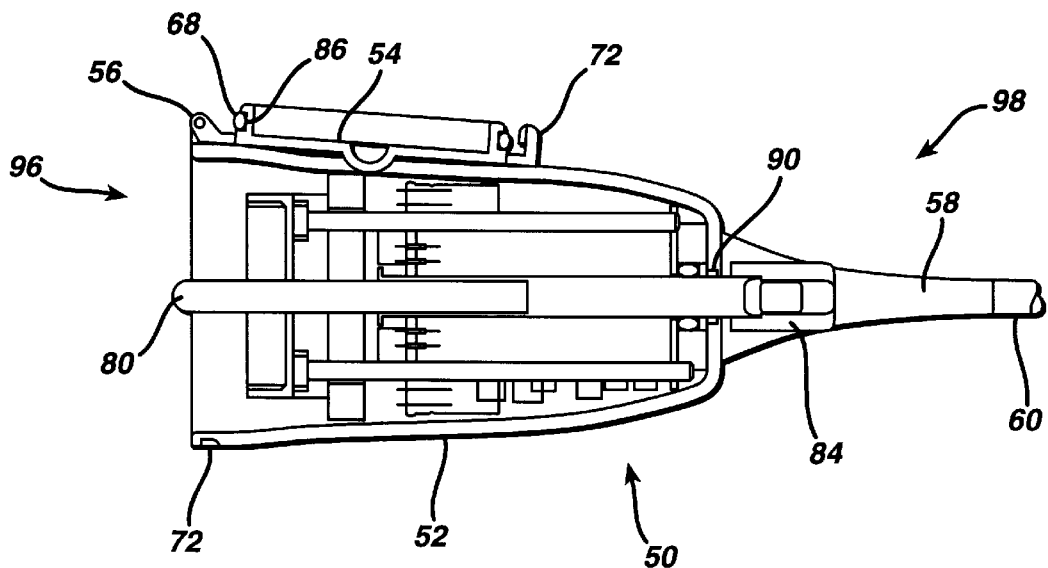
Figure 4B:
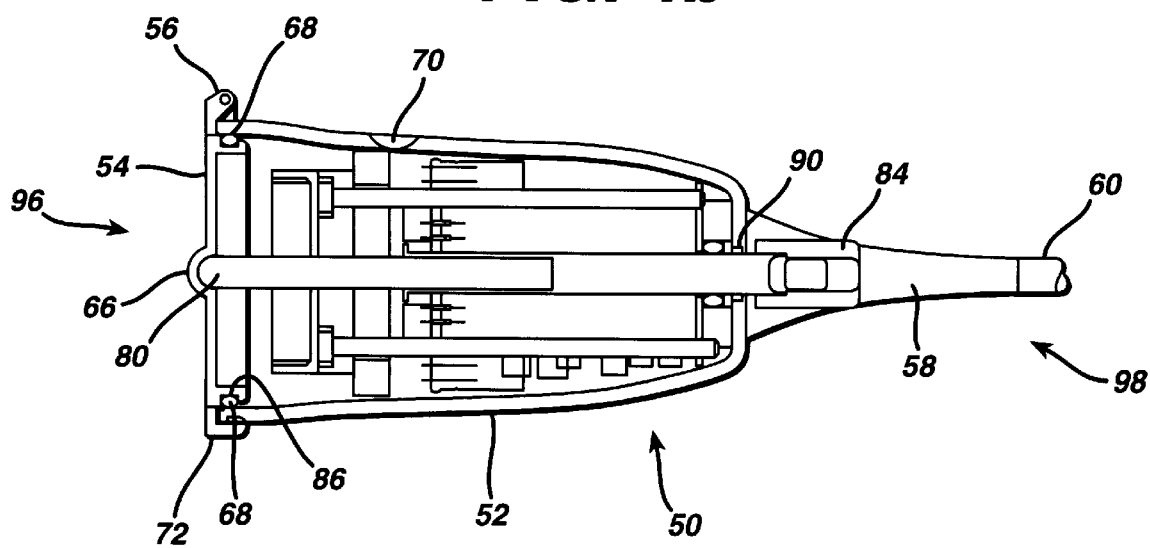

Turning now to FIGS. 4*a*–4*c*, another embodiment of the present invention is shown that solves the problem encountered when the connector is submerged in the liquid sterilization environment. End views and a top view of connector enclosure 50 are shown. Connector enclosure 50 is comprised of connector housing 52, cover 54, hinging device 56, and cable strain relief 58 with cable 60, which connects the probe to an ultrasound system (not shown).

Connector housing 52 is shown with indent 70 and cover 54 is shown with detent 66, o-ring 68, and latch 72. Connector housing 50 has a receiving end 96 and a cable end 98. Also, shown are connector shaft 80, member 82, and handle 84, which are used in other devices for sealing the connector as described above. The present invention avoids reliance on connector shaft 80 or other internal connector assembly components for sealing. Thus, the present invention is not limited to connectors that utilize a connector shaft or other latching components.

In FIG. 4*a*, cover 54 is shown in the open position. Detent 66 is matched to fit in indent 70 such that cover 54 will lay flush against connector housing 50 when cover 54 is in the open position. In FIG. 4*b*, cover 54 is shown in a closed or sealed position. It can be seen that in the closed position, the interior portion of detent 66 provides space for connector cover 54 to be closed over connector shaft 80. O-ring 68 of cover 54 provides a liquid tight seal when cover 54 is in the closed position. O-ring 68 is sized and shaped to fit in channel 86, which extends around the interior circumference of cover 54 such that a liquid tight seal is formed when cover 54 is latched with latch 72 to connector housing 52. Although o-ring 68 is shown on the inside of cover 54, o-ring 68 can also be configured to reside on the outside of connector housing 50. Cover 54 is shown configured as a male cover that mates with a female housing, however, cover 54 may be configured as a female cover that mates with a male housing.

FIGS. 4*a*–4*c*, show o-ring 90 used to form a liquid tight seal around connector shaft 80 as it protrudes from cable end 98. FIG. 4*c* shows o-ring 94 used to form a liquid tight seal around cable strain relief 58 as cable 60 protrudes from cable end 98.

Thus, the embodiments of the present invention provide a connector enclosure and housing used for protecting sensitive electronic components of the connector during the sterilization process of ultrasonic probes. Moreover, the present invention may be used on any type of ultrasonic probe and is not limited to intraoperative probes.

What is claimed is:

1. An enclosure for enclosing and sealing a connector and a portion of a cable of an ultrasonic probe assembly in a liquid tight manner when said probe is submerged in a sterilization liquid, comprising:
   a housing for enclosing said connector and said portion of said cable, wherein said housing is comprised of a top enclosure half and a bottom enclosure half, each enclosure half having opposing mating surfaces;
   a gasket compressed between said mating surfaces; and
   a latch for latching said top enclosure half to said bottom enclosure half.

2. The enclosure of claim 1, wherein said gasket is made from a resilient material.

3. The enclosure of claim 1, wherein said gasket is sized for compression between a groove circumferencially located on said mating surface of said enclosure half and a tongue circumferencially located on said mating surface of said top enclosure half.

4. The enclosure of claim 1, wherein said gasket includes a bottom sealing portion and a top sealing portion for sealing said cable in a liquid tight manner while said cable is positioned in an opening located between said top enclosure half and said bottom enclosure half.

5. The enclosure of claim 4, wherein said bottom sealing portion is affixed to said gasket and located in a notch in said bottom enclosure half.

6. The enclosure of claim 5, wherein said top sealing portion is located in a notch in said top enclosure half.

7. An enclosure for enclosing and sealing a connector and a portion of a cable of an ultrasonic probe assembly in a liquid tight manner when said probe is submerged in a sterilization liquid, comprising:
   a housing for enclosing said connector and said portion of a cable, wherein said housing is comprised of a top enclosure half and a bottom enclosure half, each enclosure half having opposing mating surfaces;
   means for sealing said mating surfaces; and a latch for latching said top enclosure half to said bottom enclosure half.

8. The housing of claim 7, wherein said sealing means is comprised of a resilient gasket.

9. The housing of claim 8, wherein said gasket includes a cable sealing portion for creating a liquid tight seal between said cable and said enclosure halves.

10. The housing of claim 9, wherein said cable sealing portion is comprised of a first and second portion.

11. The housing of claim 10, wherein said first cable sealing portion is affixed to said gasket and located in a notch on one of said enclosure halves and said second cable sealing portion is located in a notch in said opposing enclosure half.

12. An ultrasonic probe connector for enclosing and sealing connector components and a portion of a cable of an ultrasonic probe assembly in a liquid tight manner when said probe is submerged in a sterilization liquid, comprising:

a housing having a receiving end and a cable end;

a cover for sealing said receiving end in a liquid tight manner;

a latch for removably securing said cover to said housing;

a hinge for hingedly connecting said cover to said housing; and means for sealing said cable to said housing in a liquid tight manner.

13. The ultrasonic probe connector of claim 12, wherein said cover is comprised of a circumferencial channel on the interior of said cover.

14. The ultrasonic probe connector of claim 13, wherein said cover is comprised of an o-ring seated in said channel.

15. The ultrasonic probe connector of claim 12, wherein said means for sealing said cable to said connector in a liquid tight manner is comprised of a strain relief and an o-ring.

16. An enclosure for enclosing and sealing connector components and a portion of a cable of an ultrasonic probe assembly to obtain a liquid tight seal, comprising:

a housing having a receiving end and a cable end;

a cover for sealing said receiving end;

a first o-ring for sealing the circumference of said cover;

a second o-ring for sealing said cable;

a hinge for hingedly connecting said cover to said housing; and a latch for latching said cover to said housing.

17. An ultrasonic probe connector, comprising:

a housing having a receiving end and a cable end;

a cover for covering said receiving end for obtaining a liquid tight seal between said cover and said housing;

an o-ring for sealing said cable between said cable and said housing at said cable end; and a latch for latching said cover to said housing.

* * * * *